(12) United States Patent
Hill et al.

(10) Patent No.: US 10,653,464 B2
(45) Date of Patent: May 19, 2020

(54) FOOT BONE PLATE PROVIDING FIXATION AND COMPRESSION

(71) Applicant: LIFE SPINE, INC., Huntley, IL (US)

(72) Inventors: Joshua Lee Hill, Pikeville, KY (US); Daniel Predick, Chicago, IL (US)

(73) Assignee: LIFE SPINE, INC., Huntley, IL (US)

( * ) Notice: Subject to any disclaimer, the term of this patent is extended or adjusted under 35 U.S.C. 154(b) by 570 days.

(21) Appl. No.: 14/619,920

(22) Filed: Feb. 11, 2015

(65) Prior Publication Data

US 2015/0223851 A1 Aug. 13, 2015

Related U.S. Application Data

(60) Provisional application No. 61/938,849, filed on Feb. 12, 2014.

(51) Int. Cl.
*A61B 17/58* (2006.01)
*A61B 17/80* (2006.01)

(52) U.S. Cl.
CPC ...... *A61B 17/8004* (2013.01); *A61B 17/8061* (2013.01)

(58) Field of Classification Search
CPC . A61B 17/80; A61B 17/8004; A61B 17/8061; A61B 17/8085
USPC ..................................... 606/70–71, 280–299
See application file for complete search history.

(56) References Cited

U.S. PATENT DOCUMENTS

| | | | | |
|---|---|---|---|---|
| 3,593,709 A | * | 7/1971 | Halloran | A61B 17/8061 52/514 |
| 3,716,050 A | * | 2/1973 | Johnston | A61B 17/8061 606/286 |
| 4,454,876 A | * | 6/1984 | Mears | A61B 17/8066 606/280 |
| 4,565,193 A | * | 1/1986 | Streli | A61B 17/809 606/297 |
| 4,800,874 A | * | 1/1989 | David | A61B 17/8061 606/286 |
| 5,261,909 A | | 11/1993 | Sutterlin et al. | |
| 5,718,705 A | * | 2/1998 | Sammarco | A61B 17/8085 606/260 |
| 5,810,822 A | | 9/1998 | Mortier | |
| 6,283,969 B1 | * | 9/2001 | Grusin | A61B 17/1728 606/280 |
| 8,177,819 B2 | | 5/2012 | Huebner et al. | |
| 8,403,970 B1 | * | 3/2013 | Bedor | A61B 17/8033 606/280 |

(Continued)

*Primary Examiner* — Jessica Weiss
(74) *Attorney, Agent, or Firm* — Foley & Lardner LLP

(57) ABSTRACT

A foot bone plate provides both fixation of two bones or bone portions and compression across their juncture. The foot bone plate has a plurality of bone screw bores positioned to receive and hold a bone screw on both sides of the two bones/bone portions (i.e. fixation), and a lateral flange positioned to receive and hold a bone screw across the foot bones/foot bone portions juncture (i.e. compression). The foot bone plate has an elongate body having a plurality of bores along its length configured to receive and hold a bone screw generally perpendicular to the foot bone plate and into the two foot bone portions. A flange is positioned at a side of the plate and includes a bore to receive and hold a bone screw. The flange and flange bore positions and holds the bone screw such that it extends through the juncture of the two bones/bone portions.

14 Claims, 5 Drawing Sheets

(56) References Cited

U.S. PATENT DOCUMENTS

| | | | |
|---|---|---|---|
| 9,254,154 B2* | 2/2016 | Gonzalez-Hernandez | ................... A61B 17/8061 |
| 9,402,667 B2* | 8/2016 | Gonzalez-Hernandez | ................. A61B 17/8061 |
| 2003/0055429 A1* | 3/2003 | Ip | ....................... A61B 17/8085 606/284 |
| 2005/0192577 A1* | 9/2005 | Mosca | ................ A61B 17/1615 606/86 B |
| 2006/0235396 A1* | 10/2006 | Sanders | ............. A61B 17/8061 606/280 |
| 2007/0233113 A1* | 10/2007 | Kaelblein | .......... A61B 17/8061 606/71 |
| 2008/0300637 A1* | 12/2008 | Austin | .................... A61B 17/74 606/290 |
| 2009/0118769 A1* | 5/2009 | Sixto, Jr. | ............ A61B 17/8061 606/280 |
| 2010/0217327 A1* | 8/2010 | Vancelette | ......... A61B 17/8061 606/281 |
| 2010/0217328 A1* | 8/2010 | Terrill | ................ A61B 17/8061 606/286 |
| 2010/0256687 A1* | 10/2010 | Neufeld | ................. A61B 17/80 606/289 |
| 2010/0324602 A1* | 12/2010 | Huebner | ................ A61B 17/80 606/280 |
| 2013/0158608 A1* | 6/2013 | Viola | .................... A61B 17/80 606/289 |
| 2013/0172942 A1* | 7/2013 | Lewis | ................ A61B 17/8061 606/281 |
| 2014/0172020 A1* | 6/2014 | Gonzalez-Hernandez | ................... A61B 17/8085 606/281 |
| 2014/0249586 A1* | 9/2014 | Guy | ................... A61B 17/8066 606/286 |
| 2015/0359573 A1 | 12/2015 | Adams et al. | |

* cited by examiner

FOOT BONE PLATE PROVIDING FIXATION AND COMPRESSION

CROSS-REFERENCE TO RELATED APPLICATIONS

This U.S. non-provisional patent application claims the benefit of and/or priority under 35 U.S.C. § 119(e) to U.S. provisional patent application Ser. No. 61/938,849 filed Feb. 12, 2014 titled "Foot Bone Plate Providing Fixation And Compression," the entire contents of which is specifically incorporated herein by reference.

BACKGROUND OF THE INVENTION

Field of the Invention

The present invention relates to implants for fixation of human bones, and particularly to implants for fixation of bones of the foot. More particularly, the present invention relates to implants for internal fixation of calcaneus, tarsal, and metatarsal bones of the foot.

Background

There are many reasons why surgeries are performed on the bones of the foot. Some foot surgeries such as osteotomies are performed to correct angular deformities. Other foot surgeries are performed to mend a fracture, fissure or to re-align or reposition bones of the foot. In these surgical procedures and others, two bones or bone portions must be joined or otherwise secured relative to each other so as to be fixed in a desired position and, eventually fuse. This may be accomplished by a foot bone plate.

In many instances, a plate is used to bridge the joint (e.g. joint, fissure, crack or the like) between the two foot bones or bone portions. The plate is configured to extend over the two bones or bone portions and has several bores each sized and shaped to receive and hold a bone screw. When installed, the bone screws extend into the bone generally perpendicular to the plate. The plate and bone screws thus hold the two bones or bone portions in a fixed orientation.

It is often desirable, however, to first compress the two bones or bone portions together. With prior art foot bone plates, it is necessary to use added instrumentation in addition to the foot bone plate and bone screws in order to provide compression. Moreover, in some instances, fixation and compression is first achieved by a bone screw extending through the two bones/bone portions and their juncture. In these instances, all of the compression is obtained through the separate bone screw and minimal, if any, compression is obtained through the plate. The plate and screw(s) are more for additional stability and protection against plantar forces.

It is therefore evident from the above that there is a need for a better manner of providing both compression and fixation of two bones or bone portions, particularly, but not necessarily, of the foot.

It is further evident from the above that there is a need for a bone plate that provides both compression and fixation between two bones or bone portions, particularly, but not necessarily, of the foot.

SUMMARY OF THE INVENTION

The present invention is a foot bone plate, system and method of use that provides both fixation of the two bones or bone portions and compression across their juncture. The foot bone plate has a plurality of bone screw bores positioned to receive and hold a bone screw on both sides of the two foot bones/bone portions (i.e. fixation), and a side or lateral flange positioned to receive and hold a bone screw across the foot bones/foot bone portions juncture (i.e. compression).

In one form, the present foot bone plate is characterized by an elongate body having a plurality of bores along its length. The bores are configured to receive and hold a bone screw generally perpendicular to the foot bone plate and into the two foot bones/bone portions. A flange is positioned at a side of the plate and includes a bore to receive and hold a bone screw. The flange and flange bore positions and holds the bone screw such that it extends through the juncture of the two bones/bone portions.

The plate may additionally have a cutout or window positioned to view the juncture and/or provide bone graft material.

According to one method of use, the foot bone plate is placed over the two foot bones/foot bone portions and their juncture. Bone screws are positioned in the plate bores and the side flange to provide fixation and compression for fusion.

Providing a combination plate and screw as one unit obtains much greater compression.

The present plate thus overcomes the deficiencies of the prior art.

Further aspects of the present invention will become apparent from consideration of the drawings and the following description of a preferred embodiment of the invention. A person skilled in the art will realize that other embodiments of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate an embodiment of the invention, wherein.

DETAILED DESCRIPTION OF THE INVENTION

Figure 1:
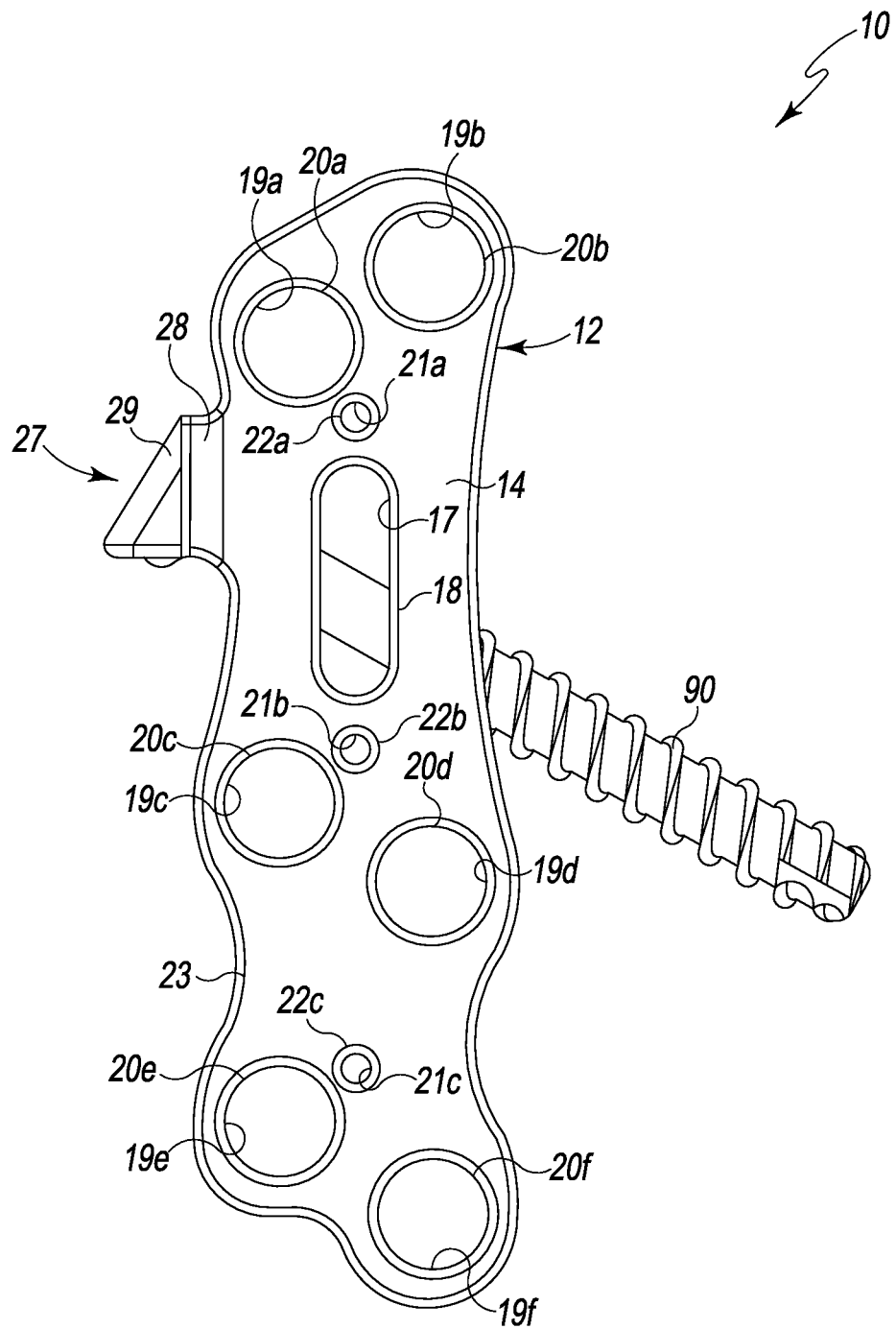
FIG. 1 is a top view of a foot bone plate fashioned in accordance with the principles of the present invention with a bone screw extending through a side flange thereof (foot bone plate system)
Figure 2:
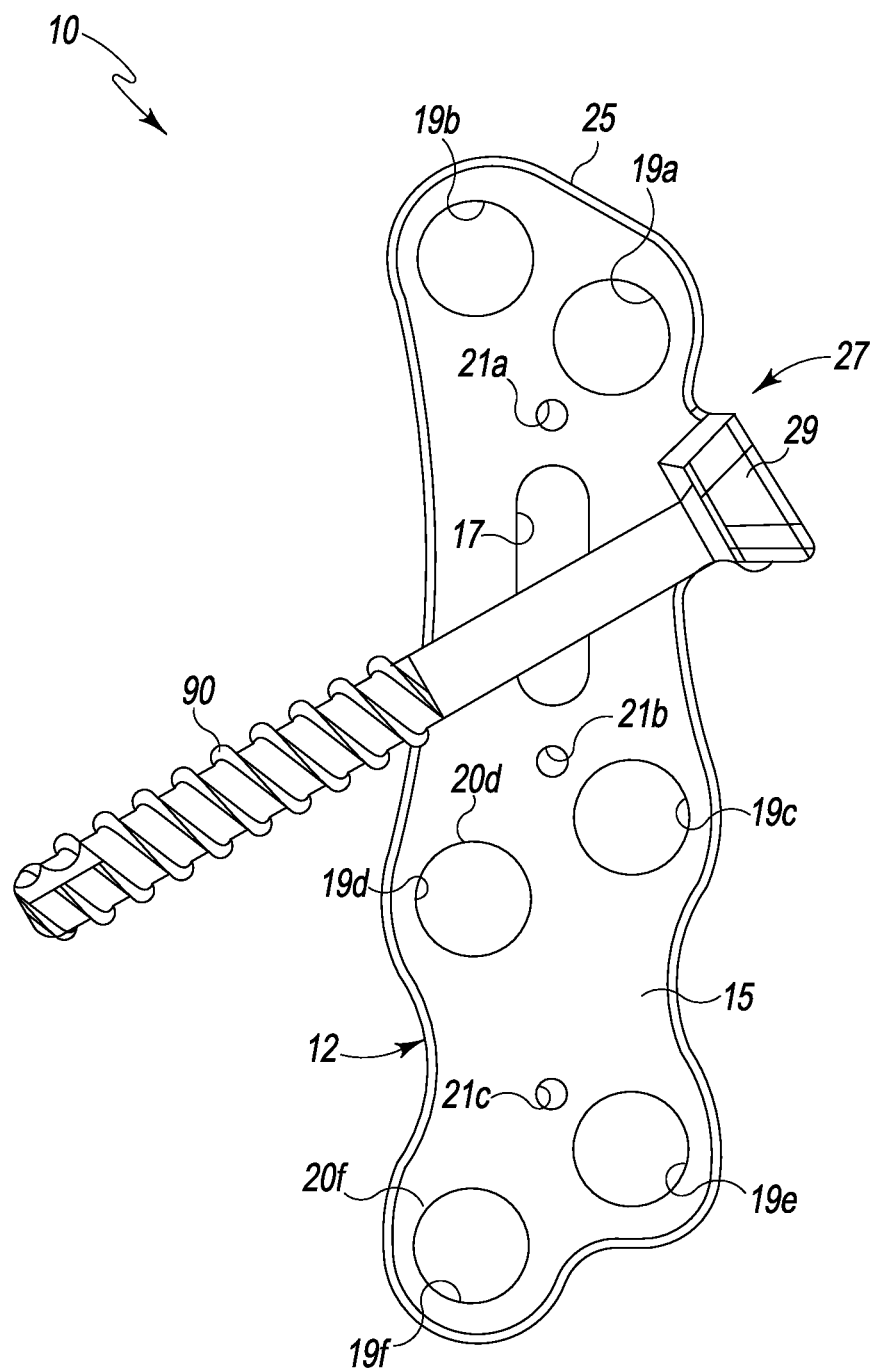
FIG. 2 is a bottom view of the foot bone plate system of FIG. 1.
Figure 3:
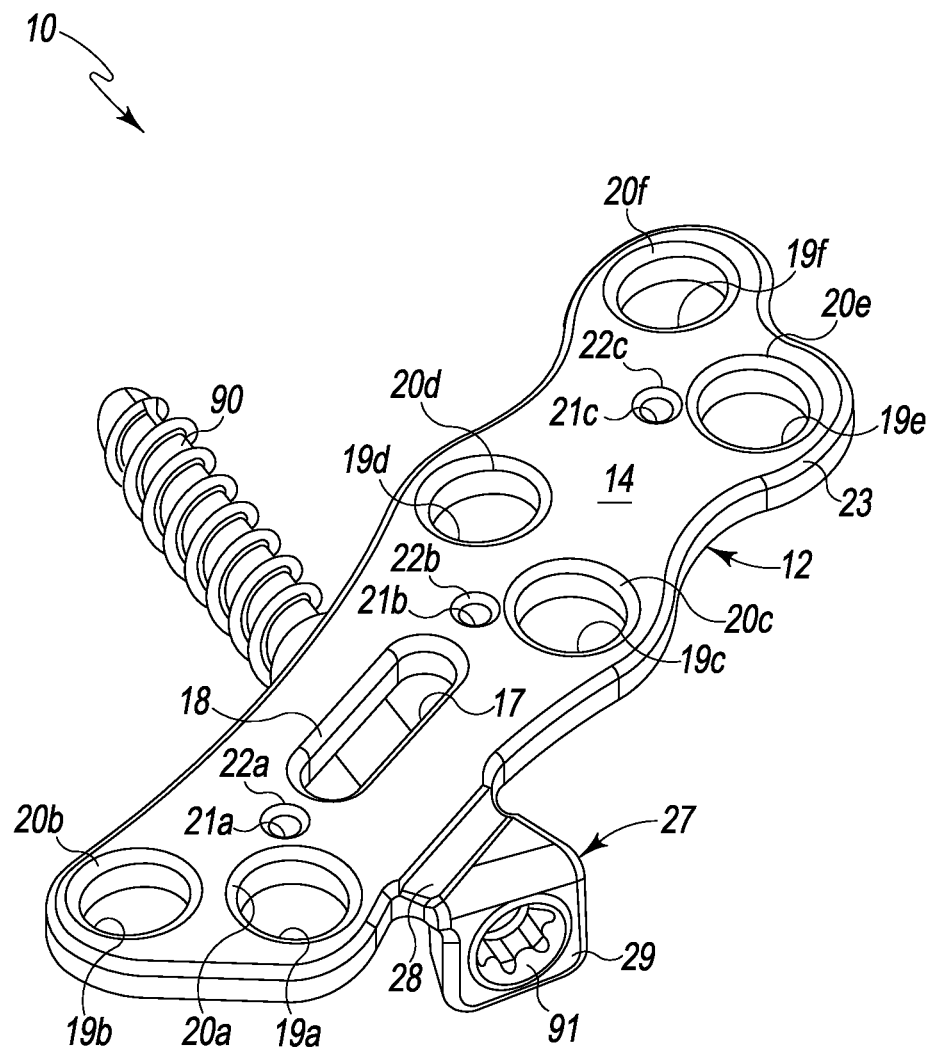
FIG. 3 is a top isometric view of the foot bone plate system of FIG. 1.

Referring to FIGS. 1-3 and 5, there is depicted a foot bone implant or system generally designated 10 (implant 10) for fixing and compressing two bones or bone portions together. The implant 10 consists of a foot bone plate or body 12 and one or more bone screws of which one exemplary bone screw 90 is shown in the figures. Other styles of bone screws may be used as appropriate. The foot bone plate 12 and bone screws 90 are fashioned from a known biocompatible implant material and is used for aiding or providing internal fixation of calcaneus, tarsal, and metatarsal bones of the foot in cases such as, but not limited to, filling an osteotomy or expanding and correcting an angular deformity in the foot. Other uses such as use on other bones/bone portions of the body are contemplated.

The foot bone plate 12 has a generally elongated polygonal-shape defining an upper surface 14 and a lower surface 15. The periphery 23 of the upper surface 14 is preferably, but not necessarily, angled or tapered downwardly from the upper surface 14 to its peripheral sides to provide a bevel. Likewise, the periphery 25 of the lower surface 15 is preferably, but not necessarily, angled or tapered downwardly from the lower surface to its peripheral side to provide a bevel. The plate 12 is sized for use in the bones of the foot. However other sizes are contemplated to accommodate various anatomies and bones. Moreover, the plate 12 may have a different polygonal shape if desired. It should be appreciated that the foot bone plate 12 and/or its principles are applicable to other bones of the body such as, but not limited to, the bones of the hand. In general, the plate 12 has first and second lateral sides, and first and second ends, the nomenclature first and second being arbitrary.

The plate 12 has six (6) bores or holes 19a-f each of which is generally cylindrical and dimensioned to receive a bone screw 90 such that the head of the bone screw is held by the plate 12 with the shank of the bone screw extending beyond the plate 12 for receipt in a foot bone/foot bone portion. The bone screw bores 19a-f each have an angled or beveled rim 20a-f on the upper surface 14 of the plate 12. The angled rims 20a-f allow a bone screw 90 to be somewhat countersunk relative to the plate by receiving the angled bone screw head, and to allow bone screw angulation. The bone screw bores 19a, 19b form a pair of bone screw bores for placing two bone screws into one foot bone/foot bone portion. The bone screw bores 19a, 19b are staggered relative to one another. The bone screw bores 19c, 19d form another pair of bone screw bores for placing two bone screws into another (second) foot bone/foot bone portion. The bone screw bores 19c, 19d are likewise staggered relative to one another. The bone screw bores 19e, 19f form yet another pair of bone screw bores for placing two more bone screws into the second foot bone/foot bone portion. The bone screw bores 19e, 19f are also staggered relative to one another. The plate 12 may have more or less bone screw bores without departing from the invention, and plate dimensions accordingly. Moreover, the positions of the bone screw bores may change if desired.

A cutout or window 17 is provided in the plate 12 between the bone screw bore pairs 19a, 19b and the bone screw bore pairs 19c, 19d and 19e, 19f. While the window 17 is shown as oval-shaped, the window 17 may take other forms and dimensions as desired. An angled or beveled rim 18 extends about the window 17 on the upper surface 14 of the plate 12. The window 17 provides access to the two foot bones/bone portions juncture or junction. As such, the window 17 may be used for providing bone graft material to the two foot bones/bone portions juncture and/or for other purposes such as providing a viewing window. The window also allows viewing of the positioning of a bone screw 90 relative to the plate 12 when installed (and as shown).

The plate 17 further includes three (3) holes or bores 21a-c that are generally cylindrical and spaced along the length of the plate 17 and generally along the longitudinal axis thereof. The first hole 21a is positioned proximate to a first longitudinal end of the plate 17 where the bone screw bores 19a and 19b are positioned. The second hole 21b is positioned proximate the middle of the plate 17 near where the bone screw bores 19c and 19d are positioned, while the third hole 21c is positioned proximate to a second longitudinal end of the plate 17 where the bone screw bores 19e and 19f are positioned. It should be appreciated that the nomenclature first, second and third is arbitrary. The bores 21a-c each have an angled or beveled rim 22a-c on the upper surface 14 of the plate 12. The holes 21a-c allow temporary fixation pins to be inserted into the bone(s) in order to hold the plate 12 in place for installing the bone screws, or to compress or distract off of.

Figure 4:
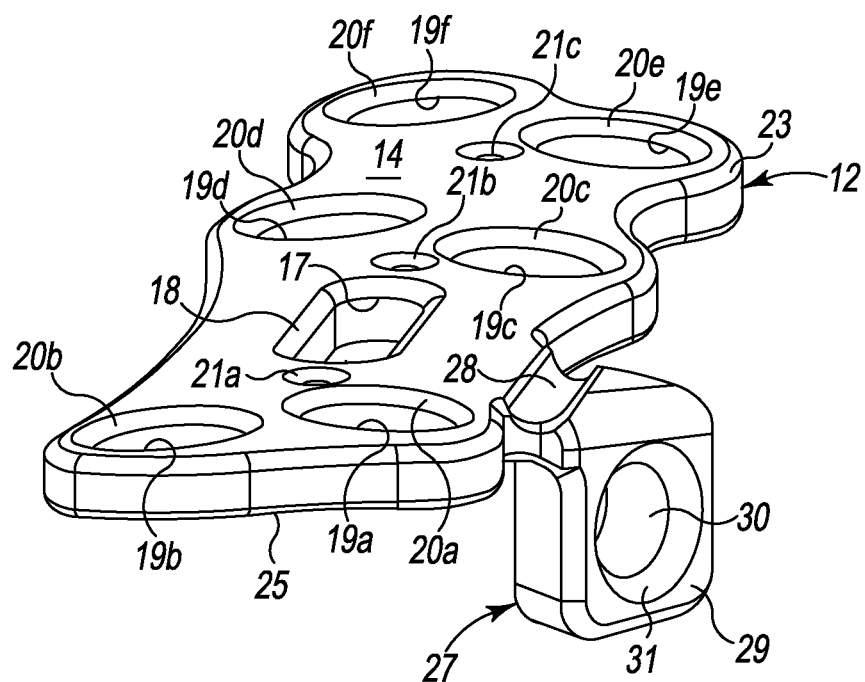
FIG. 4 is an end isometric view of the foot bone plate system of FIG. 3.

The plate 12 further includes a flange structure (flange) 27 provided at or on a lateral or lower side of the plate 12 proximate the first longitudinal end of the plate, and particularly proximate the bone screw bore 19a. The flange structure 27 is characterized by a neck 28 that extends or projects from the lateral side of the plate 12, and a flange 29 situated at the end of the neck 28. Other configurations may be used. The flange 29 extends generally downward and perpendicular relative to the lower surface 15 of the plate 12. The flange 29 has a bore 30 that extends through the flange 29 and includes a bevel 31 about the bore 30 on the face of the flange 29 (see, e.g., FIG. 4). The flange 29 and bore 30 are positioned to hold a bone screw 90 generally transverse to a plane defined by the plate (see, e.g., FIGS. 1-3) or transverse to the axes of the six (6) cylindrical bores 19a-f of the plate 12. Particularly, the flange structure 27 holds a bone screw 90 skew relative to the longitudinal axis of the plate such that the bone screw 90 will extend through the first and second bones/bone portions and thus their juncture. The amount of skew may be varied relative to that shown as long as it passes through the bone juncture. In this manner, the bone screw 90 allows the two bones/bone portions to be compressed together.

Figure 5:
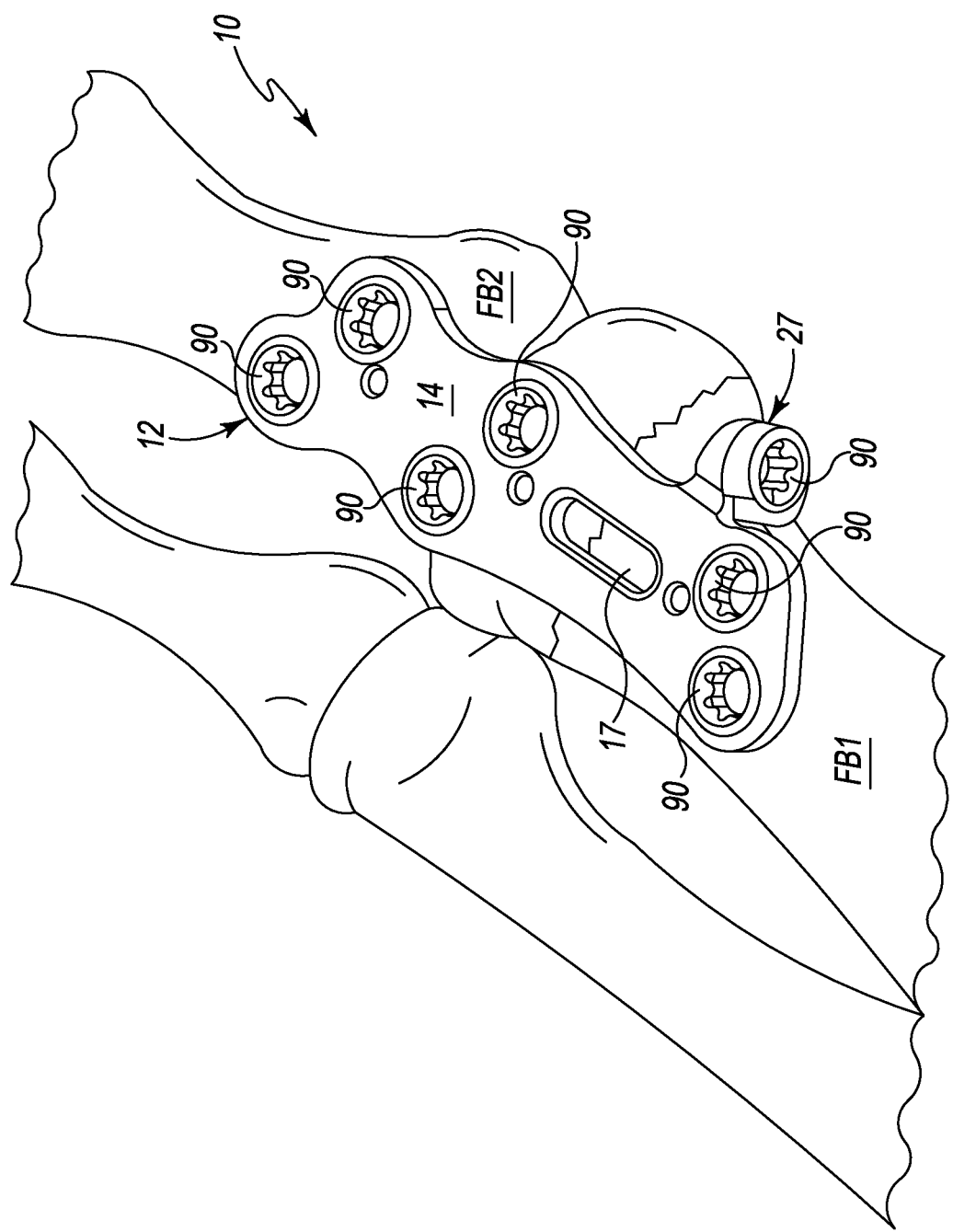
FIG. 5 is an illustration of the foot bone plate of FIGS. 1-4 installed on two adjacent bone/bone portions of a foot.

Referring to FIG. 5, there is shown an exemplary illustration of the present foot bone implant 10 installed on two adjacent foot bones FB1 and FB2 of a foot. The implant 10 has been mounted or attached to the foot bones FB1 and FB2 and over a fracture (shown as a jagged line) in the foot bone FB1. While one use is shown in FIG. 5, the present implant 10 may be used in various situations. The plate 12 of the implant 10 is positioned onto the foot bone FB1 and attached thereto by bone screws 90. A bone screw 90 is likewise provided in the flange 27 and into and through the foot bones FB1 and FB2 and their juncture (here shown as the fracture). The bone screw of the flange 27 provides compression between the fracture (juncture) of the foot bones FB1, FB2. The plate 12 and bone screws 90 thereof provide fixation of the foot bones FB1, FB2 to each other.

It should be appreciated that although the present bone fixation implant/plate system has been described in particularity with respect to foot bones, it is applicable to hand bones and those bones being very similar in anatomy. It should also be appreciated that dimensions of the plate 12 and its components and/or features can be altered as desired.

What is claimed is:

1. An implant for fixing and compressing two adjacent bone portions across their juncture, the implant comprising:
an elongate body defining a longitudinal axis and having an upper surface, a lower surface opposite the upper surface; a first lateral side, a second lateral side opposite the first lateral side, a first end, and a second end opposite the first end;
a plurality of cylindrical bores in the elongate body, at least one of the cylindrical bores having a first axis that extends between the upper surface of the elongate body and the lower surface of the elongate body, the plurality of cylindrical bores situated along the elongate body from the first end to the second end thereof, each cylindrical bore configured to receive and hold a bone screw in one of the two adjacent bone portions; and a flange having a first portion and a second portion, the first portion extending from the first lateral side of the elongate body, the first portion comprising a neck having a recessed surface between the upper surface of the elongate body and the second portion of the flange, the second portion of the flange extending generally perpendicular to the lower surface of the elongate body and having a first surface, a second surface opposite the first surface, and a cylindrical bore with a second axis that extends between the first and second surfaces of the second portion;

wherein the first axis is generally perpendicular to the first longitudinal axis;

wherein the second axis extends at an oblique angle relative to the longitudinal axis of the elongate body so that a bone screw received in the cylindrical bore of the flange extends into the two adjacent bone portions and across their juncture;

wherein the longitudinal axis, the first axis, and the second axis are offset to each other and do not intersect; and wherein bone screws used in the plurality of cylindrical bores of the elongate body provide fixation of the elongate body to the two adjacent bone portions, wherein a bone screw used in the cylindrical bore of the flange provides compression of the two adjacent bone portions across their juncture.

2. The implant of claim 1, further comprising:
a cutout in the elongate body that extends between the upper surface of the elongate body and the lower surface of the elongate body, and situated proximate to the flange.

3. The implant of claim 2, wherein the plurality of cylindrical bores in the elongate body includes two cylindrical bores proximate the first end of the elongate body, two cylindrical bores proximate the second end of the elongate body, and two cylindrical bores between the first and second ends of the elongate body.

4. The implant of claim 3, wherein the first lateral side of the elongate body has a first length, and the second lateral side of the elongate body has a second length that is greater than the first length of the first lateral side.

5. The implant of claim 4, further comprising:
a first rim extending continuously about and beveled between the upper surface of the elongate body adjacent the first lateral side of the elongate body, the first end of the elongate body, the second lateral side of the elongate body, and the second end of the elongate body; and
a second rim extending continuously about and beveled between the lower surface of the elongate body adjacent the first lateral side of the elongate body, the first end of the elongate body, the second lateral side of the elongate body, and the second end of the elongate body.

6. The implant of claim 5, further comprising a bevel situated in the upper surface of the elongate body about each one of the plurality of cylindrical bores in the elongate body.

7. The implant of claim 1, wherein the elongate body further defines a longitudinal third axis between the first and second ends, and wherein the third axis is at an acute angle relative to the second axis.

8. A method of providing fixation and compression of first and second adjacent bone portions of the foot, the method comprising:

providing an implant per claim 1;
installing the implant of claim 1 onto the first and second bone portions of adjacent bone portions via bone screws through the cylindrical bone screw bores of the plate; and
installing a bone screw through the flange of the plate, and into the first and second bone portions of the adjacent bone portions and through their juncture.

9. An implant for fixing and compressing two adjacent foot bone portions across their juncture, the implant comprising:

an elongate plate defining an upper surface, a lower surface opposite the upper surface; a first lateral side, a second lateral side opposite the first lateral side, a first end between the first lateral side and the second lateral side, and a second end opposite the first end and between the first lateral side and the second lateral side, wherein the elongate plate further defines a longitudinal first axis between the first and second ends;

a first pair of cylindrical bores in the elongate plate, each cylindrical bore having a second axis that extends between the upper surface of the elongate plate and the lower surface of the elongate plate and situated proximate the first end of the elongated plate, the first pair of cylindrical bores each configured to receive and hold a bone screw in one of the two adjacent foot bone portions;

a second pair of cylindrical bores in the elongate plate, each cylindrical bore having a third axis that extends between the upper surface of the elongate plate and the lower surface of the elongate plate and situated proximate the second end of the elongated plate, the second pair of cylindrical bores each configured to receive and hold a bone screw in another of the two adjacent foot bone portions; and a flange having a first portion and a second portion, the first portion extending from the first lateral side of the elongate plate, the first portion comprising a neck having a recessed surface between the upper surface of the elongate plate and the second portion of the flange, the second portion of the flange extending from the first portion and generally perpendicular to the lower surface of the elongate plate, the second portion having a cylindrical bore with a fourth axis;

wherein the second and third axes are generally perpendicular to the first axis, wherein the fourth axis extends at an oblique angle relative to, and at an acute angle relative to, the longitudinal first axis of the elongate plate, wherein the longitudinal first axis, the second axis, the third axis, and the fourth axis are offset to each other and do not intersect, and wherein the cylindrical bore of the flange is configured to receive and hold a bone screw into the two adjacent foot bone portions and across their juncture; and wherein bone screws used in the first and second pairs of cylindrical bores of the elongate plate provide fixation of the elongate plate to the two adjacent foot bone portions, while a bone screw used in the cylindrical bore of the flange provides compression of the two adjacent foot bone portions across their juncture.

10. The implant of claim 9, further comprising:
a cutout in the elongate plate that extends between the upper surface of the elongate plate and the lower surface of the elongate plate, and situated proximate to the flange.

11. The implant of claim 10, further comprising a third pair of cylindrical bores in the elongate plate, each one of which has an axis that extends between the upper surface of the elongate plate and the lower surface of the elongate plate and situated between the first pair of cylindrical bores in the elongate plate and the second pair of cylindrical bores in the elongate plate, wherein bone screws used in the third pair of cylindrical bores of the elongate plate provide fixation of the elongate plate to one of the two adjacent foot bone portions.

12. The implant of claim 11, wherein the first lateral side of the elongate plate has a first length, and the second lateral side of the elongate plate has a second length that is greater than the first length of the first lateral side.

13. The implant of claim 12, further comprising:
   a first rim extending continuously about and beveled between the upper surface of the elongate plate adjacent the first lateral side of the elongate plate, the first end of the elongate plate, the second lateral side of the elongate plate, and the second end of the elongate plate; and
   a second rim extending continuously about and beveled between the lower surface of the elongate plate adjacent the first lateral side of the elongate plate, the first end of the elongate plate, the second lateral side of the elongate plate, and the second end of the elongate plate.

14. The implant of claim 13, further comprising a bevel situated in the upper surface of the elongate plate about the first, second, and third pairs of cylindrical bores in the elongate plate.

* * * * *